May 29, 1973 J. M. GARABEDIAN Plant Pat. 3,345
APRICOT TREE
Filed Aug. 9, 1971
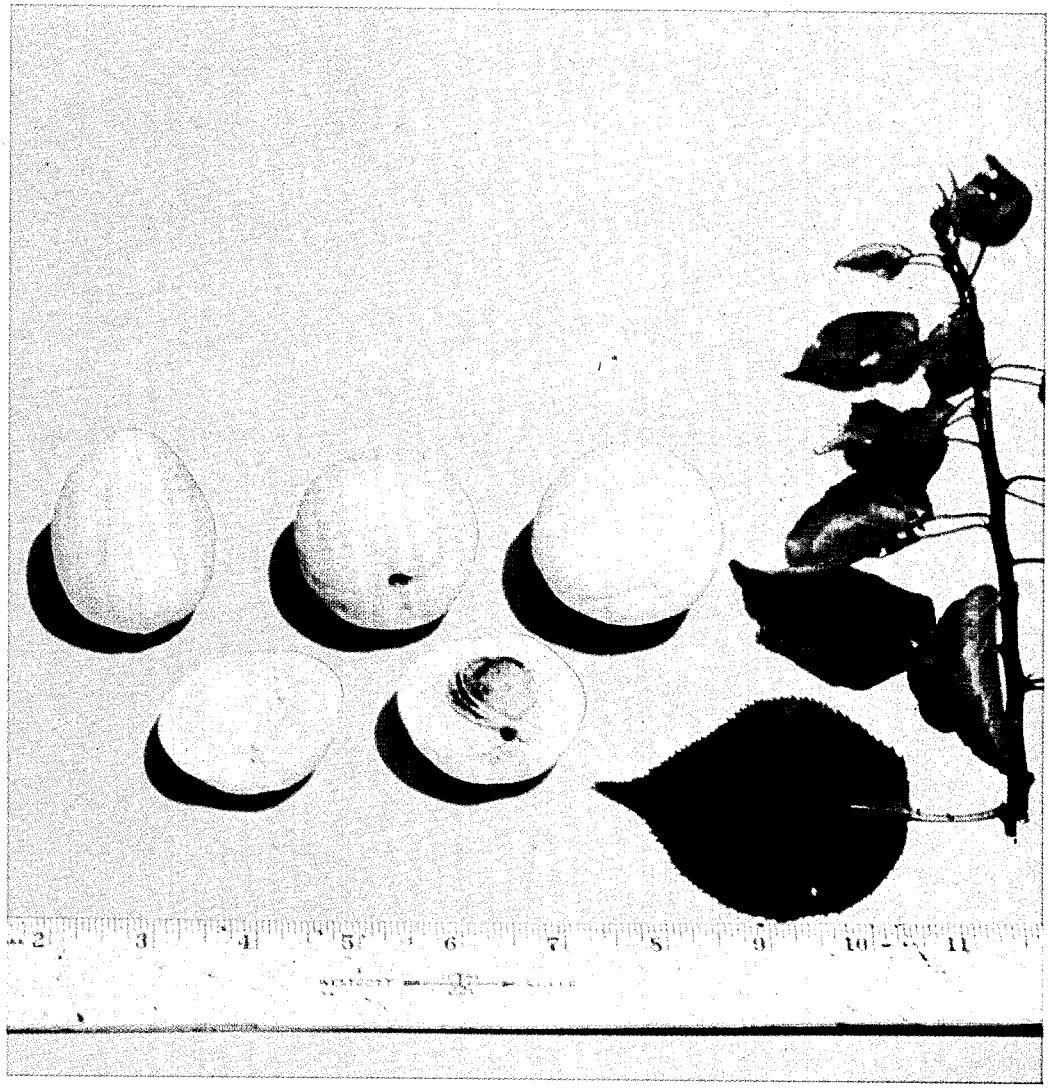

United States Patent Office

Plant Pat. 3,345
Patented May 29, 1973

3,345

APRICOT TREE

John M. Garabedian, Fresno, Calif., assignor to Superior Farming Company

Filed Aug. 9, 1971, Ser. No. 170,394
Int. Cl. A01h 5/03
U.S. Cl. Plt.—39 1 Claim

ABSTRACT OF THE DISCLOSURE

An apricot tree which is of medium size, vigorous, upright, open, vase formed, hardy, and a regular and productive bearer of uniform, large, early ripening, firm fleshed fruit which is of good shipping, keeping and eating quality; the fruit being further characterized by its ability to remain on the tree for a substantial period of time without impairment of its commercial quality, and additionally characterized by skin which is golden yellow to golden overlaid to a substantial extent with a pinkish-red blush.

ORIGIN OF THE VARIETY

The present variety of apricot tree was originated by me, on a ranch (of which I am an owner) located near Fresno, Fresno County, Calif. as an open-pollinated seedling of the Blenheim-Royal (unpatented). More particularly, seeds of the Blenheim-Royal were gathered and planted on the aforesaid ranch in connection with a plant breeding program which I conduct. The seedlings, resulting from such planting, were maintained by me under careful and continuing observation, and—when such seedlings began to bear fruit—one of such seedlings, and which is the present variety, evidenced certain new and distinctive characteristics and which made the variety desirable for commercial growing. I, therefore, selected such one seedling for asexual reproduction preparatory to commercialization of the variety.

ASEXUAL REPRODUCTION OF THE VARIETY

I asexually reproduced the present variety of apricot tree by budding the same, on Nemaguard peach rootstock, on the aforesaid ranch. In maturity, such asexual reproductions ran true to the original tree in all respects.

SUMMARY OF THE VARIETY

The present variety of apricot tree is of medium size, vigorous, upright, open, vase formed, hardy, and a regular and productive bearer of uniform, large, early ripening, firm fleshed fruit which is of good shipping, keeping (long shelf life), and eating quality; the fruit ripening approximately thirty days before the Blenheim-Royal.

The present variety of apricot tree is further characterized by the ability of the fruit to remain on the tree for a substantial period of time without impairment of its commercial quality.

The present variety of apricot tree is additionally characterized by fruit whose skin is golden yellow to golden overlaid to a substantial extent with a very attractive pinkish-red blush.

BRIEF DESCRIPTION OF THE DRAWING

The drawing is an illustration, by photographic reproduction in color, showing fruit and leaves of the variety.

DESCRIPTION OF THE VARIETY

The botanical details of this new and distinct variety of apricot tree—with color definitions (except those in common color terms) referenced to Maerz and Paul Dictionary of Color—are as follows:

Tree:
- *Size.*—Medium.
- *Vigor.*—Vigorous.
- *Growth.*—Upright.
- *Density.*—Open.
- *Form.*—Vase formed.
- *Hardiness.*—Hardy.
- *Production.*—Productive.
- *Bearing.*—Regular bearer.

Trunk:
- *Size.*—Medium.
- *Texture.*—Medium, many vertical striations in bark.
- *Color.*—Brown to reddish brown.

Branches:
- *Size.*—Medium.
- *Texture.*—Medium, glossy.
- *Color.*—Current season's growth: red on dorsal side, green on ventral side. One-year wood: Grey over brown (15–H–11). Two-year wood: Brown to reddish brown.

Lenticels:
- *Number.*—Numerous.
- *Size.*—Small.

Leaves:
- *Size.*—Medium, length—7.2 cm. to 8.7 cm.—average 7.9 cm., width—5.5 cm. to 7 cm.—average 6.2 cm.
- *Form.*—Ovate to orbicular with acuminate apex tip. Young leaves at growing tips more ovate, with acuminate tip. On young shoots of current season's growth, leaves more narrow and elongated with reddish color, also found on woody stems and on leaf petiole.
- *Thickness.*—Medium.
- *Texture.*—Smooth, glabrous.
- *Leaf apex.*—Acutely pointed.
- *Leaf color.*—Dorsal side—Medium green (23–J–8); ventral side—Medium green (23–L–6).
- *Leaf base.*—Base angle usually obtuse, few acute.
- *Leaf veins.*—Pinnately net veined.
- *Margin.*—Crenate, glandular.
- *Petiole.*—Length: medium, average length—2.5 cm. Thickness: Slender, average thickness—1 mm. Color: Dorsal side—Red (54–k–6); ventral side—Light green to reddish green. Red on petiole extends into main leaf vein on both sides of mature leaves.
- *Glands.*—Number—0 to 4, usually 1 or 2; opposite, small, globose, positioned on base of leaf bud and on petiole; mostly red—mixed green and red on leaf margins.
- *Stipules.*—None.
- *Leaf buds.*—Small, pointed.

Flower Buds:
- *Hardness.*—Half hardy.
- *Size.*—Small.
- *Length.*—Short.
- *Form.*—Plump, free.
- *Texture.*—Glabrous.

Flowers:
- *Blooming period.*—Early.
  Dates of first and full bloom: Feb. 25, 1971, and Mar. 4, 1971, respectively.
- *Size.*—Small.
- *Petals.*—Size and form uneven.
- *Color.*—Whitish pink.

Fruit:
- *Maturity when described.*—Eating hard.
- *Date of first picking* (Fresno County, Calif.).—May 27, 1971.
- *Date of last picking* (Fresno County, Calif.).—June 15, 1971.

*Size.*—Uniform, large, average in longitudinal section—1⅝″; average in cross section—1½″.

*Form.*—Uniform, slightly unsymmetrical, globose to oblong—many conical to roundish oblong, mostly round-oblate, compressed laterally, longitudinal section form—roundish oblong, transverse through diameter—mostly ablong, some irregular, halves slightly unequal. High shoulder on ventral side at base, and at apex on dorsal side gives oblique appearance.

*Suture.*—Distinct, shallow, extends from base to beyond but discontinues at apex, with slight depression at pistil point.

*Ventral surface.*—Rounded strongly, lipped throughout dorsal side, lips equal.

*Cavity.*—Rounded, abrupt, small, slightly elongated in suture plane, with suture showing on one side, average depth—¼″, average breadth—3/16″, markings—some furrows and creases about cavity.

*Base.*—Rounded to truncate.

*Apex.*—Short, truncate, apical.

*Stem.*—Small, average length—8 mm., average width—4 mm.

Skin:

*Thickness.*—Thin.

*Texture.*—Medium.

*Flavor.*—Slightly bitter.

*Tenacity.*—Tenacious to flesh.

*Tendency to crack.*—None in dry season.

*Color.*—Golden yellow (9–I–6) to golden (10–J–7), overlaid to a substantial extent with a pinkish red blush.

*Down.*—Scant, short, does not roll up when rubbed.

Flesh:

*Color.*—Yellowish orange (10–L–10), surface of pit cavity—yellow (10–K–8 to 11–L–8).

*Amygdalin.*—Abundant.

*Juice.*—Scant.

*Texture.*—Firm, fine, meaty.

*Fibers.*—Few, fine, tender.

*Ripens.*—Evenly.

*Flavor.*—Acid—mostly sharp.

*Aroma.*—Wanting.

*Eating quality.*—Good.

Stone:

*Type.*—Semifree to cling, adheres to flesh over entire surface, but mostly along both dorsal and ventral edges.

*Fibers.*—Short, retains short fiber-like threads along ridges.

*Size.*—Large to medium, average length—2.6 cm., average breadth—2.4 cm., average thickness—1.2 cm.

*Form.*—Elliptical to ovoid, full cuneate toward base.

*Base.*—Straight.

*Hilum.*—Narrow, oval to oblong—mostly cupped.

*Apex.*—Rounded.

*Sides.*—Equal, but thinner on ventral edge.

*Surface.*—Irregularly furrowed, ridged near base, pitted throughout on both sides of stone—very fine—stipuled.

*Ridges.*—Jagged on dorsal side—grooves shallow, interrupted on ventral side, continuous on dorsal side.

*Ventral edge.*—Thin, with wing toward apex.

*Dorsal edge.*—Full, with shallow broad groove throughout.

*Color.*—Golden wheat (11–D–7).

*Thickness of pit wall.*—Average ⅛″–3/16″.

*Tendency to split.*—None.

*Kernel.*—Roundish-ovate, bitter, viable, average width—12 mm., average length—15 mm., pellicle color—Golden Wheat (11–C–7), with brownish stipuled dots on surface, and with undercolor stripes running from base to apex, Amygdalin—abundant.

Use: Market, dessert, culinary, shipping.

Keeping quality: Good.

Shipping quality: Good.

The apricot tree and its fruit herein described may vary in slight detail due to climatic and soil conditions under which the variety may be grown; the present description being of the variety as grown in the Central Valley of California.

I claim:

1. A new and distinct variety of apricot tree, substantially as illustrated and described, which is of medium size, vigorous, upright, open, vase formed, hardy, and a regular and productive bearer of uniform, large, firm fleshed fruit of good shipping, keeping, and eating quality, and having golden yellow to yellow skin overlaid to a substantial extent with a pinkish-red blush; the fruit ripening approximately thirty days before the Blenheim-Royal, and being capable of remaining on the tree for a substantial period without impairment of its commercial quality.

No references cited.

ROBERT E. BAGWILL, Primary Examiner